United States Patent
Zhao et al.

(10) Patent No.: US 8,374,723 B2
(45) Date of Patent: Feb. 12, 2013

(54) OBTAINING FORCE INFORMATION IN A MINIMALLY INVASIVE SURGICAL PROCEDURE

(75) Inventors: Wenyi Zhao, Mountain View, CA (US); Tao Zhao, Sunnyvale, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 557 days.

(21) Appl. No.: 12/428,108

(22) Filed: Apr. 22, 2009

(65) Prior Publication Data
US 2010/0168918 A1   Jul. 1, 2010

Related U.S. Application Data

(60) Provisional application No. 61/204,083, filed on Dec. 31, 2008.

(51) Int. Cl.
*G01L 5/00* (2006.01)
*G06F 19/00* (2011.01)
*H04N 5/00* (2011.01)

(52) U.S. Cl. ........ 700/259; 700/245; 700/253; 700/254; 700/260; 702/41; 318/568.11; 318/568.16; 318/568.17; 382/128; 382/153

(58) Field of Classification Search .................. None
See application file for complete search history.

(56) References Cited

U.S. PATENT DOCUMENTS

| | | | | |
|---|---|---|---|---|
| 4,362,977 A | * | 12/1982 | Evans et al. .................. 700/254 |
| 5,086,401 A | * | 2/1992 | Glassman et al. .............. 700/259 |
| 5,193,963 A | * | 3/1993 | McAffee et al. ................ 414/5 |
| 5,239,246 A | * | 8/1993 | Kim .......................... 318/568.11 |
| 5,299,288 A | * | 3/1994 | Glassman et al. ............. 700/245 |
| 5,408,409 A | * | 4/1995 | Glassman et al. ............. 600/407 |
| 5,619,180 A | | 4/1997 | Massimino et al. |
| 5,762,458 A | * | 6/1998 | Wang et al. .................... 414/1 |
| 6,028,409 A | * | 2/2000 | Wierda ........................ 318/568.1 |
| 6,125,385 A | | 9/2000 | Wies et al. |

(Continued)

FOREIGN PATENT DOCUMENTS

| | | |
|---|---|---|
| EP | 1285634 A1 | 2/2003 |
| WO | WO2008/049898 * | 5/2008 |

OTHER PUBLICATIONS

Khünapfel et al., CAD-Based Simulation and Modelling for Endoscopic Surgery, 1995, Minimally Invasive Therapy, vol. 4, No. 5/6, pp. 336-339.*

(Continued)

*Primary Examiner* — Thomas Black
*Assistant Examiner* — Sara Lewandroski

(57) ABSTRACT

Methods of and a system for providing force information for a robotic surgical system. The method includes storing first kinematic position information and first actual position information for a first position of an end effector; moving the end effector via the robotic surgical system from the first position to a second position; storing second kinematic position information and second actual position information for the second position; and providing force information regarding force applied to the end effector at the second position utilizing the first actual position information, the second actual position information, the first kinematic position information, and the second kinematic position information. Visual force feedback is also provided via superimposing an estimated position of an end effector without force over an image of the actual position of the end effector. Similarly, tissue elasticity visual displays may be shown.

40 Claims, 12 Drawing Sheets

U.S. PATENT DOCUMENTS

| | | | |
|---|---|---|---|
| 6,233,504 B1 * | 5/2001 | Das et al. | 700/260 |
| 6,366,272 B1 | 4/2002 | Rosenberg et al. | |
| 6,385,509 B2 * | 5/2002 | Das et al. | 700/260 |
| 6,424,885 B1 * | 7/2002 | Niemeyer et al. | 700/245 |
| 6,459,926 B1 * | 10/2002 | Nowlin et al. | 600/429 |
| 6,493,608 B1 | 12/2002 | Niemeyer | |
| 6,522,906 B1 * | 2/2003 | Salisbury et al. | 600/407 |
| 6,659,939 B2 * | 12/2003 | Moll et al. | 600/102 |
| 6,671,581 B2 * | 12/2003 | Niemeyer et al. | 700/245 |
| 7,155,315 B2 | 12/2006 | Niemeyer et al. | |
| 7,373,219 B2 | 5/2008 | Nowlin et al. | |
| 7,443,115 B2 * | 10/2008 | Okamoto et al. | 318/100 |
| 7,778,733 B2 | 8/2010 | Nowlin et al. | |
| 2003/0040758 A1 | 2/2003 | Wang et al. | |
| 2004/0106916 A1 | 6/2004 | Quaid et al. | |
| 2005/0200324 A1 * | 9/2005 | Guthart et al. | 318/568.11 |
| 2006/0106493 A1 | 5/2006 | Niemeyer et al. | |
| 2006/0142657 A1 | 6/2006 | Quaid et al. | |
| 2006/0241414 A1 | 10/2006 | Nowlin et al. | |
| 2006/0258938 A1 | 11/2006 | Hoffman et al. | |
| 2006/0293643 A1 | 12/2006 | Wallace et al. | |
| 2007/0021738 A1 | 1/2007 | Hasser et al. | |
| 2007/0038080 A1 | 2/2007 | Salisbury, Jr. et al. | |
| 2009/0088897 A1 | 4/2009 | Zhao et al. | |
| 2009/0192523 A1 | 7/2009 | Larkin et al. | |
| 2009/0192524 A1 | 7/2009 | Itkowitz et al. | |
| 2010/0168763 A1 | 7/2010 | Zhao et al. | |
| 2010/0168919 A1 | 7/2010 | Okamoto | |

OTHER PUBLICATIONS

Preusche et al., Teleoperation Concepts in Minimal Invasive Surgery, Nov. 2002, Control Engineering Practice, vol. 10, Issue 11, pp. 1245-1250.*

Khunapfel et al., CAD-Based simulation and modeling for endoscopic surgery, 1995, Minimally Invasive Therapy, vol. 4, No. 5/6, pp. 336-339.*

Wang et al., Vision-Based Sensing of Forces in Elastic Objects, 2001, Sensors and Actuators, vol. 94, Issue 3, pp. 142-156.*

Akinbiyi, Takintope, "Intelligent Instruments and Visual Force Feedback in Laparascopic Minimally Invasive Surgery," Master's Thesis, The Johns Hopkins University, Baltimore, Maryland, 2005, 103 pages.

Reiley, Carol Elizabeth: "Evaluation of Augmented Reality Alternatives to Direct Force Feedback in Robot-Assisted Surgery: Visual Force Feedback and Virtual fixtures," Master of Science thesis, The Johns Hopkins University, Baltimore, Maryland, Apr. 2007, 184 pages.

Reiley, Carol E. et al., "Effects of visual force feedback on robot-assisted surgical task performance," Journal of Thoracic and Cardiovascular Surgery, Jan. 2008, pp. 196-202.

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

PCT/US09/68406 International Search Report and Written Opinion of the International Searching Authority, mailed Mar. 24, 2010, 11 pages.

* cited by examiner

US 8,374,723 B2

OBTAINING FORCE INFORMATION IN A MINIMALLY INVASIVE SURGICAL PROCEDURE

CROSS REFERENCE TO RELATED APPLICATIONS

This non-provisional application claims the benefit under 35 U.S.C. §119(e) of provisional U.S. Pat. App. No. 61/204,083 (filed Dec. 31, 2008), which is incorporated herein by reference.

This application is related to non-provisional U.S. patent application Ser. No. 12/428,142 [entitled "Visual Force Feedback in a Minimally Invasive Surgical Procedure"] (concurrently filed) and to provisional U.S. Pat. App. No. 61/204,085 (filed Dec. 31, 2008), both of which are incorporated herein by reference.

BACKGROUND

Minimally invasive surgical (MIS) procedures have become more common using robotic (e.g., telerobotic) surgical systems. One example of such a system is the Minimally invasive robotic surgery system described in commonly owned U.S. Pat. No. 7,155,315 (filed Dec. 12, 2005), entitled "Camera Referenced Control in a Minimally Invasive Surgical Apparatus."

A common form of minimally invasive surgery is endoscopy. Endoscopic surgical instruments in minimally invasive medical techniques generally include an endoscope for viewing the surgical field and working tools defining end effectors. The working tools are similar to those used in conventional (open) surgery, except that the working end or end effector of each tool is separated from its handle by an approximately 12-inch long extension tube. Typical surgical end effectors include clamps, graspers, scissors, staplers, or needle holders, as examples.

To manipulate end effectors, a human operator, typically a surgeon, manipulates or otherwise commands a locally provided master manipulator. Commands to the master manipulator are translated as appropriate and sent to a slave manipulator that could be remotely deployed. The slave manipulator then moves the end effector according to the user's commands.

In order to duplicate the "feel" of actual surgery, force feedback may be included in minimally invasive robotic surgical systems. To provide such feedback, conventional systems have the remote slave manipulator feed back force information to the master manipulator, and that force information is utilized to provide haptic feedback to the surgeon so that the surgeon feels as if he or she is manipulating the end effectors directly by hand.

SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment, a method of providing force information for a robotic surgical system is provided. The method includes storing first kinematic position information and first actual position information for a first position of an end effector; moving the end effector via the robotic surgical system from the first position to a second position; storing second kinematic position information and second actual position information for the second position; and providing force information regarding force applied to the end effector at the second position utilizing the first actual position information, the second actual position information, the first kinematic position information, and the second kinematic position information.

In accordance with another embodiment, a method of providing force information for a robotic surgical system is provided. The method includes storing first kinematic position information from joint states of a linkage while the linkage supports an end effector at a first position; storing first visual position information from a first image of the end effector captured while the end effector is at the first position; and providing force information regarding force applied to the end effector at the first position utilizing a first offset between the first kinematic position information and the first visual position information.

In accordance with yet another embodiment, an assembly for providing force information within a robotic system is provided. The assembly includes a first input for first kinematic position information from joint states of a linkage while the linkage supports an end effector at a first position; a second input for actual position information; and a module coupled with the first input and the second input, the module providing force information regarding force applied to the end effector at the first position in response to the first kinematic position information and the first visual position information.

In accordance with still another embodiment, a system of providing a visual representation of force information in a robotic system is provided. The system includes an image input for receiving an image of an end effector while a force is applied to the end effector; a display coupled to the image input so as to present an actual position of the end effector under the applied force; and a processor coupled to the display, the processor generating a second image representing a projected position of the end effector offset from the first position so as to visually indicate the force, the processor transmitting the second image to the display so that the second image is superimposed with the first image.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Figure 1:
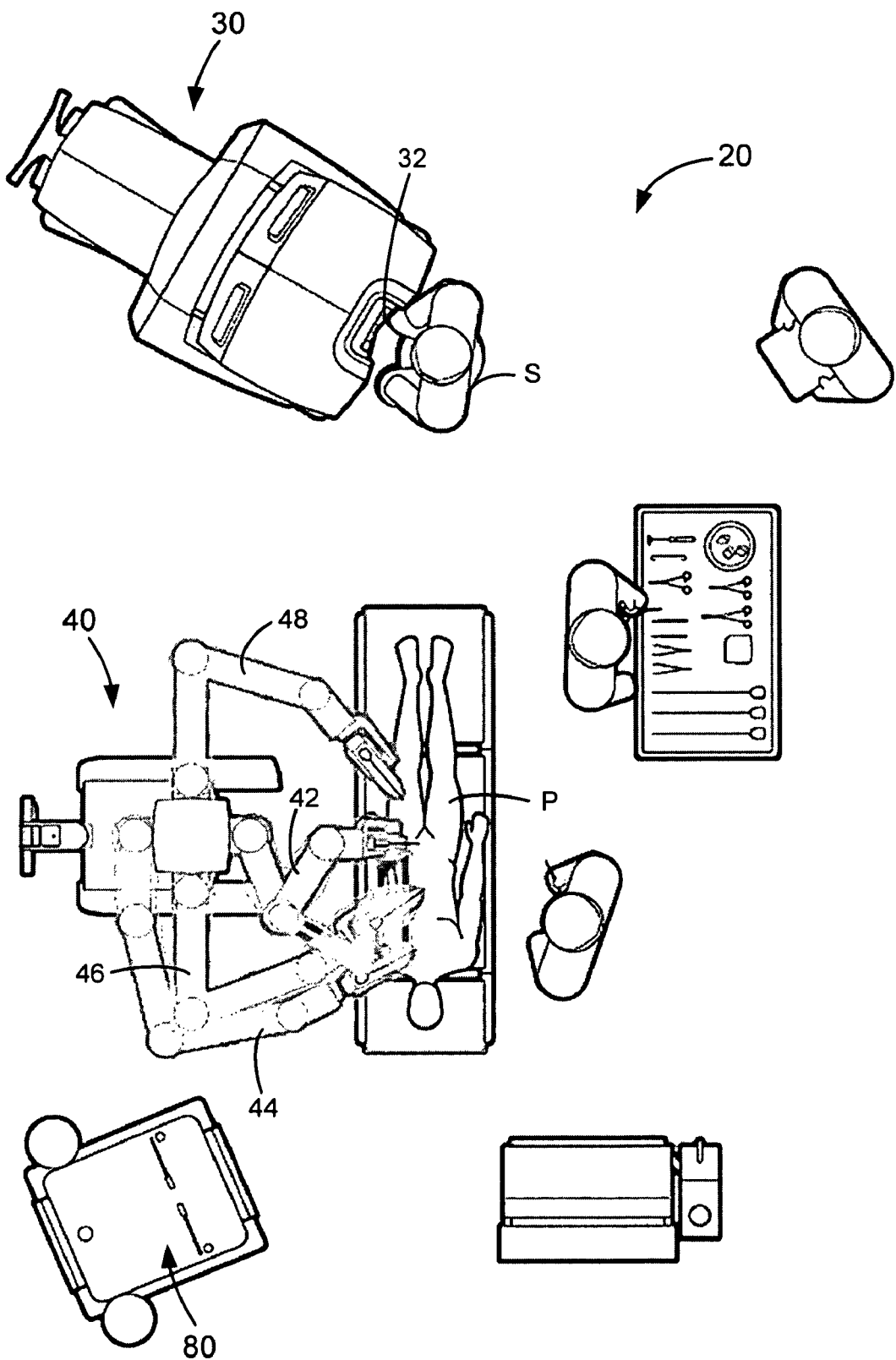
FIG. 1 shows a top view of an operating room which includes a minimally invasive telesurgical system in accordance with an embodiment.
Figure 10:
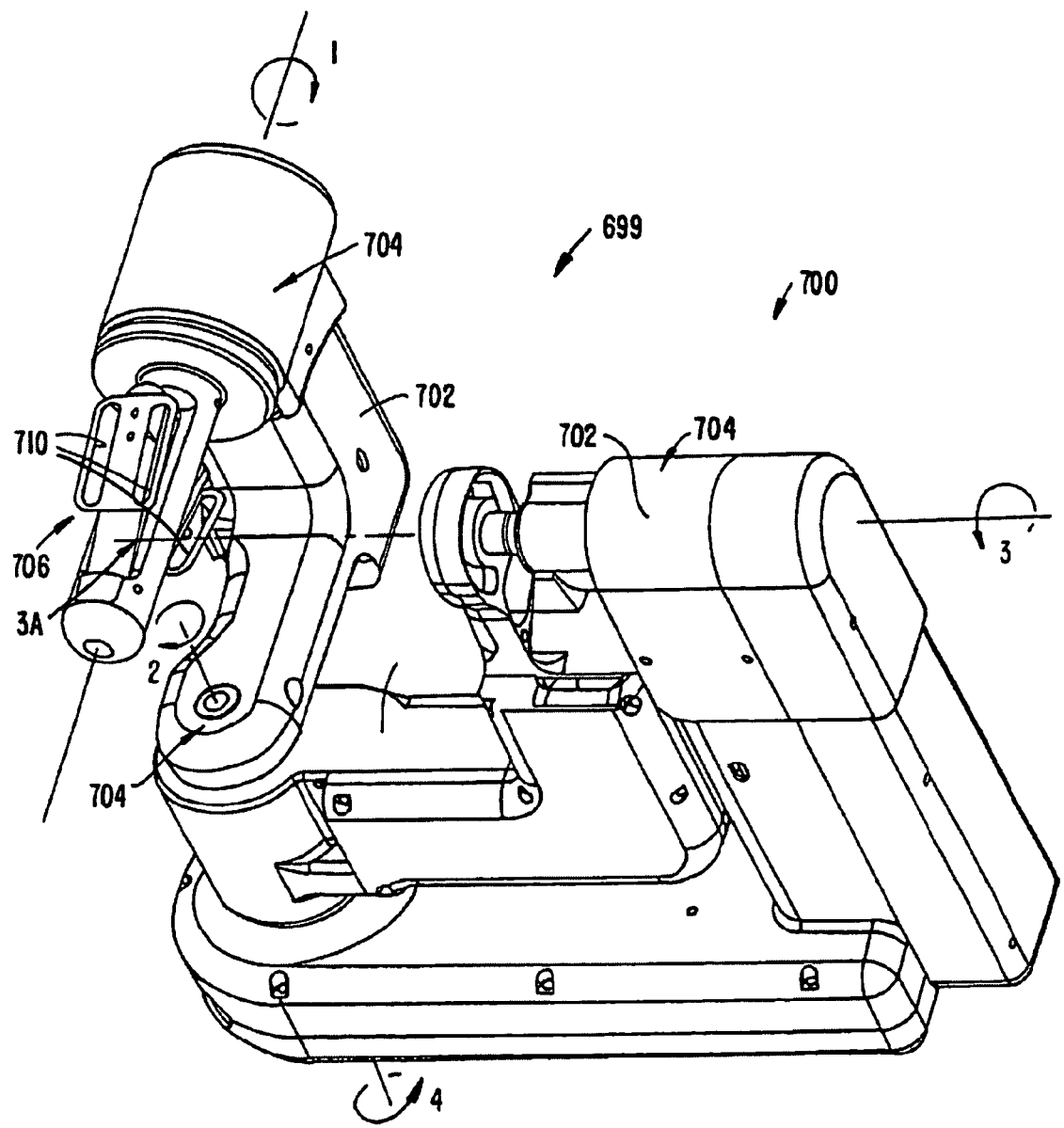
FIG. 10 is a side perspective view of a master controller in accordance with an embodiment.

Referring now to the drawings, in which like reference numerals represent like parts throughout several views, FIG. 1 shows a minimally invasive telesurgical system 20 having an operator station or surgeon console 30 in accordance with an embodiment. The surgeon console 30 includes a viewer 32 where an image of a surgical site is displayed to a surgeon S. As is known, a support (not shown) is provided on which the surgeon S can rest his or her forearms while gripping two master controls 700 (FIG. 10), one in each hand. More controls may be provided if more end effectors are available, but typically a surgeon manipulates only two controls at a time and, if multiple end effectors are used, the surgeon releases one end effector with a master control 700 and grasps another with same master control. When using the surgeon console 30, the surgeon S typically sits in a chair in front of the surgeon console, positions his or her eyes in front of the viewer 32, and grips the master controls 700, one in each hand, while resting his or her forearms on the support.

A patient side cart 40 of the telesurgical system 20 is positioned adjacent to a patient P. In use, the patient side cart 40 is positioned close to the patient P requiring surgery. The patient side cart 40 typically is stationary during a surgical procedure, and it includes wheels or castors to render it mobile. The surgeon console 30 is typically positioned remote from the patient side cart 40 and may be separated from the patient side cart by a great distance, even miles away, but will typically be used within the same operating room as the patient cart.

Figure 2:
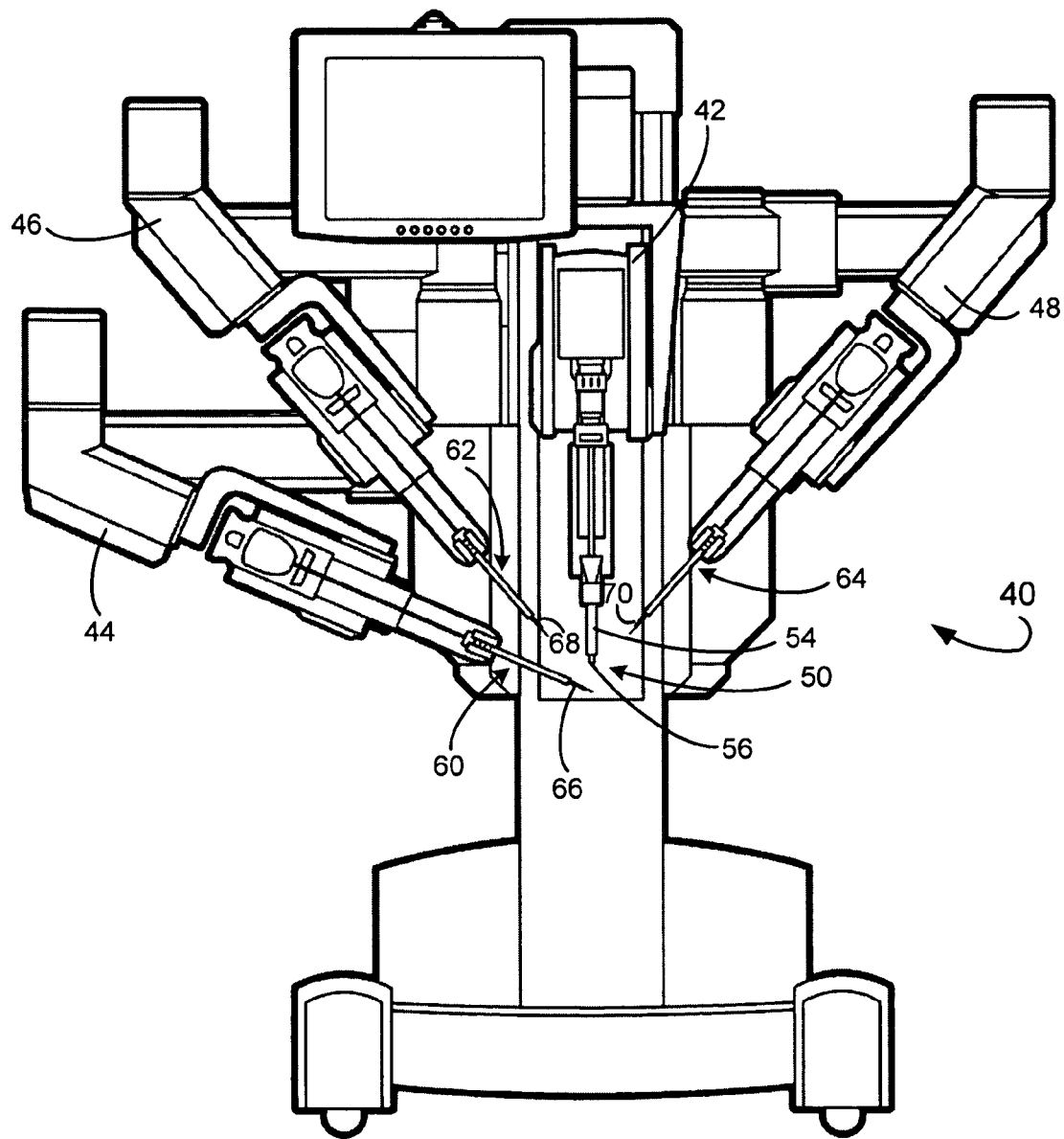
FIG. 2 is front view of a patient cart for the minimally invasive telesurgical system of FIG. 1.

The patient side cart 40, shown in more detail in FIG. 2, typically includes two or more robotic arm assemblies. Each arm assembly typically includes unpowered, lockable "set up" joints and powered "manipulator" joints. In the embodiment shown in FIG. 2, the patient side cart 40 includes four robotic arm assemblies 42, 44, 46, 48, but more or fewer may be provided. Each robotic arm assembly 42, 44, 46, 48 is normally operatively connected to one of the master controls of the surgeon console 30. Thus, movement of the robotic arm assemblies 42, 44, 46, 48 is controlled by manipulation of the master controls.

One of the robotic arm assemblies, indicated by the reference numeral 42, is arranged to hold an image capturing device 50, e.g., an endoscope, or the like. The endoscope or image capturing device 50 includes a viewing end 56 at a remote end of an elongate shaft 54. The elongate shaft 54 permits the viewing end 56 to be inserted through a surgery entry port of the patient P. The image capturing device 50 is operatively connected to the viewer 32 of the surgeon console 30 to display an image captured at its viewing end 56.

Each of the other robotic arm assemblies 44, 46, 48 includes a surgical instrument or tool 60, 62, 64, respectively. The tools 60, 62, 64 of the robotic arm assemblies 44, 46, 48 include end effectors 66, 68, 70, respectively. The end effectors 66, 68, 70 are mounted on wrist members which are pivotally mounted on distal ends of elongate shafts of the tools, as is known in the art. The tools 60, 62, 64 have elongate shafts to permit the end effectors 66, 68, 70 to be inserted through surgical entry ports of the patient P. Movement of the end effectors 66, 68, 70 relative to the ends of the shafts of the tools 60, 62, 64 is also controlled by the master controls of the surgeon console 30. The instruments are typically removably attached to the manipulator arms, and a mechanical interface between the instrument and the arm transmits actuating forces to the instrument.

The telesurgical system 20 includes a vision cart 80. In an embodiment, the vision cart 80 includes most of the "core" computer equipment or other controls for operating the telesurgical system 20. As an example, signals sent by the master controllers of the surgeon console 30 may be sent to the vision cart 80, which in turn may interpret the signals and generate commands for the end effectors 66, 68, 70 and/or robotic arm assemblies 44, 46, 48. In addition, video sent from the image capturing device 50 to the viewer 34 may be processed by, or simply transferred by, the vision cart 80. In other embodiments, "core" computer equipment for the telesurgical system may be distributed in the surgeon console and patient side cart.

Figure 3:
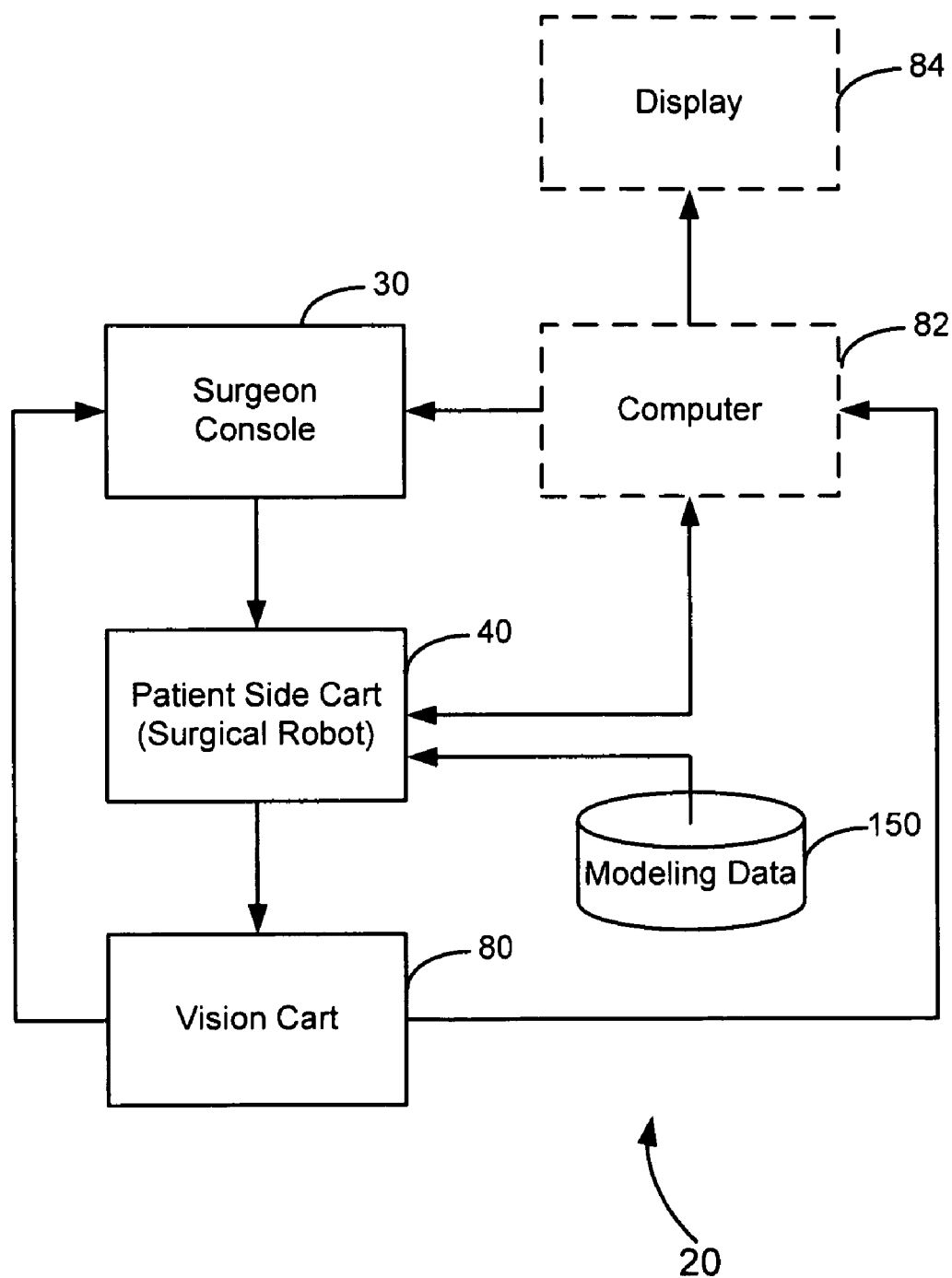
FIG. 3 is a block diagram representing components of the minimally invasive telesurgical system of FIG. 1.

FIG. 3 is a diagrammatic representation of the telesurgical system 20. As can be seen, the system includes the surgeon console 30, the patient side cart 40, and the vision cart 80. In addition, in accordance with an embodiment, an additional computer 82 and display 84 are provided. These components may be incorporated in one or more of the surgeon console 30, the patient side cart 40, and/or the vision cart 80. For example, the features of the computer 82 may be incorporated into the vision cart 80. In addition, the features of the display 84 may be incorporated into the surgeon console 30, for example, in the viewer 32, or maybe provided by a completely separate display or the surgeon console or on another location. In addition, in accordance with an embodiment, the computer 82 may generate information that may be utilized without a display, such as the display 84.

Although described as a "computer," the computer 82 may be a component of a computer system or any other software or hardware that is capable of performing the functions herein. Moreover, as described above, functions and features of the computer 82 may be distributed over several devices or software components. Thus, the computer 82 shown in the drawings is for the convenience of discussion, and it may be replaced by a controller, or its functions may be provided by one or more components.

Figure 4:
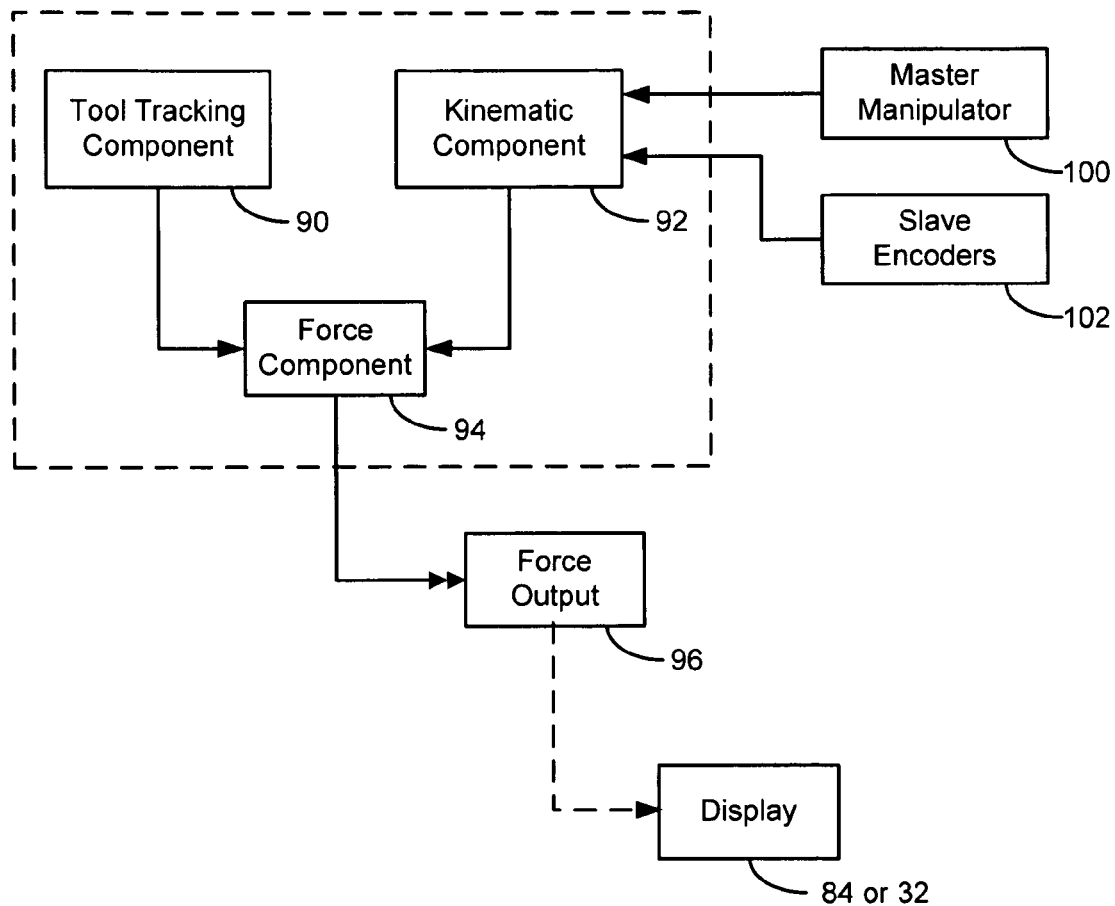
FIG. 4 is a block diagram representing components for a computer for use in the minimally invasive telesurgical system of FIG. 1 in accordance with an embodiment.

FIG. 4 shows components of the computer 82 in accordance with an embodiment. In the embodiment shown in the drawing, the computer 82 includes a tool tracking component 90, a kinematic component 92, and a force component 94. Briefly described, the tool tracking component 90 and kinematic component 92 provide information to the force component 94. The force component 94 combines or otherwise utilizes this information and outputs a force output 96.

A positional component is included in or is otherwise associated with the computer 82. The positional component provides information about a position of an end effector, such as one of the end effectors 66, 68, 70. In the embodiment shown in the drawings, the tool tracking component 90 is the positional component, and it provides information about a position of an end effector, such as the end effectors 66, 68, 70. By "position," we mean at least one of the location and/or the orientation of the end effector. A variety of different technologies may be used to provide information about a position of an end effector, and such technologies may or may not be considered tool tracking devices. In a simple embodiment, the positional component utilizes video feed from the image capturing device 50 to provide information about the position of an end effector, but other information may be used instead of, or in addition to, this visual information, including sensor information, kinematic information, any combination of these, or additional information that may provide the position and/or orientation of the end effectors 66, 68, 70. Examples of systems that may be used for the tool tracking component 90 are disclosed in U.S. Pat. App. Pub. No. US 2006/0258938, entitled, "Methods and System for Performing 3-D Tool Tracking by Fusion of Sensor and/or Camera Derived Data During Minimally Invasive Robotic Surgery"; U.S. Pat. No. 5,950,629 (filed Apr. 28, 1994), entitled "System for Assisting a Surgeon During Surgery"; U.S. Pat. No. 6,468,265 (filed Nov. 9, 1999), entitled "Performing Cardiac Surgery Without Cardioplegia"; and U.S. Pat. App. Pub. No. US 2008/0004603 A1 (filed Jun. 29, 2006), entitled "Tool Position and Identification Indicator Displayed in a Boundary Area of a Computer Display Screen." In accordance with an embodiment, the tool tracking component 90 utilizes the systems and methods described in commonly owned U.S. Pat. App. No. 61/203,975 (filed Dec. 31, 2008), which is incorporated herein by reference. In general, the positional component maintains information about the actual position and orientation of end effectors. This information is updated depending upon when the information is available, and may be, for example, asynchronous information.

To manipulate the tools 60, 62, 64, each of the slave manipulators in the robotic arm assemblies 42, 44, 46, 48 is conventionally formed of linkages that are coupled together and manipulated through motor controlled joints. These slave manipulators are linked to movement of the master manipulators or controls 100 (FIG. 4). Since the construction and operation of such robotic manipulators are well known, their details need not be repeated here. For example, general details on robotic manipulators of this type can be found in John J. Craig, Introduction to Robotics Mechanics and Control, 2nd edition, Addison-Wesley Publishing Company, Inc., 1989.

The kinematic component 92 is generally any device that estimates a position, herein a "kinematic position," of an end effector utilizing information available through the telesurgical system 20. In an embodiment, the kinematic component 92 utilizes kinematic position information from joint states of a linkage to the end effector. As an example, the kinematic component 92 may utilize the master/slave architecture for the telesurgical system 20 to calculate intended Cartesian positions of the end effectors 66, 68, 70 based upon encoder signals (from encoders 102, FIG. 4) for the joints in the linkage for each of the tools 60, 62, 64. An example of a kinematic system is described in U.S. Pat. No. 7,155,315, although others may be utilized.

As is known, during movement of a linkage, a master controller provides instructions, for example via the vision cart 80, to the slave manipulators to cause corresponding movement of the robot. The instructions provide a position (herein "command position") in which the master manipulators direct the slave manipulators. This command position is the position at which the tool or end effector is ideally located as instructed by the master manipulator, and it would be the actual position if there were no errors in the joints and no flexing in the components of the linkage.

In reality, however, an end effector or tool may be in a different location than the command position, either initially or after a sequence of moves by the slave manipulator. In some telesurgical systems, detected joint positions, provided by the encoders 102, may provide information about an estimated position of end effector (herein an "encoder-detected position" of the end effector). The difference between the command position and the encoder-detected position may be used to generate a joint position or kinematic error, and torque commands may be provided for correcting the position of the end effector from the encoder-detected position to the command position, in the form of a correction.

If a joint correction is made for joint position error as described above, then the new corrected position of the end effector is referred to herein as the "corrected position." This corrected position is not necessarily aligned with the command position, because there may be errors in the stiffness of the joints or the readings of the encoders. In addition, even if the joints were aligned perfectly, there may be some flexion in the components of the linkage, causing the actual position of end effector to not completely align with the control position.

Figure 5:
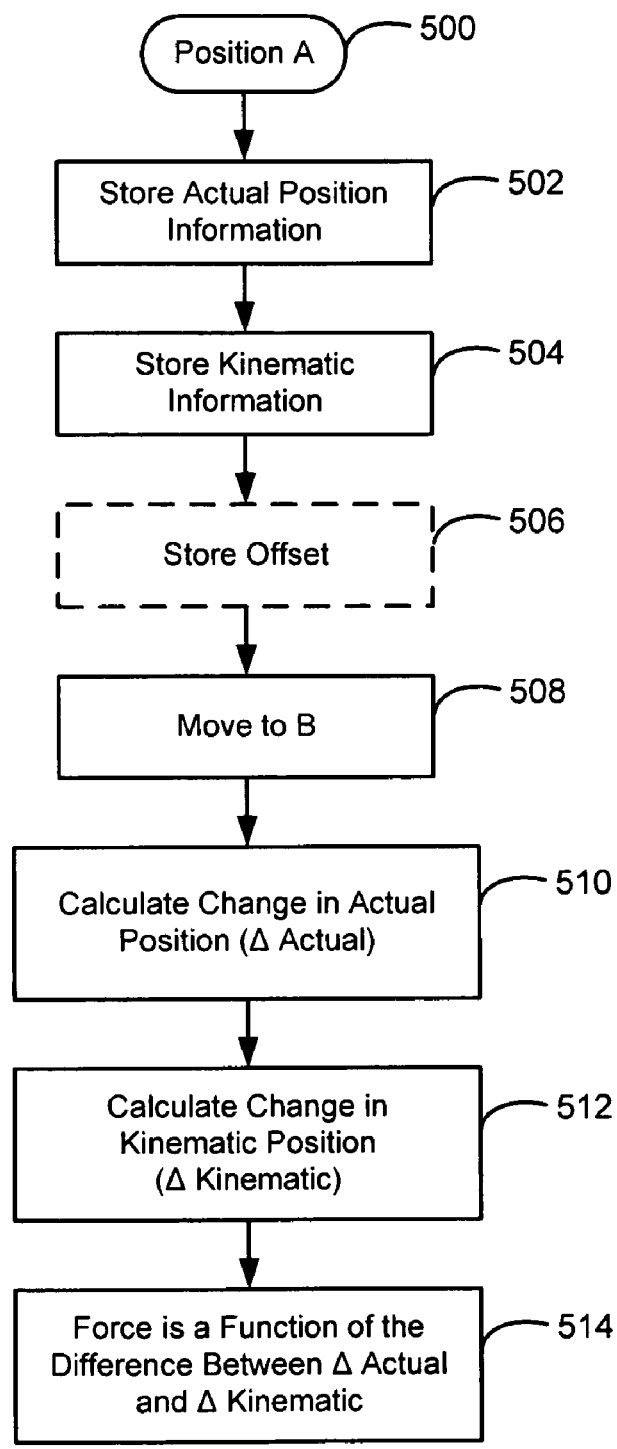
FIG. 5 is a flowchart representing steps for calculating force on an end effector in accordance with an embodiment.

FIG. 5 is a flowchart representing steps for calculating force on an end effector in accordance with an embodiment. In accordance with this embodiment, a comparison is made between a kinematic position of the end effector versus an actual position of the end effector, and such comparison represents force on the end effector. In such an embodiment, the kinematic position may be the corrected position, if used, or the encoder-detected position. Since forces applied to the tool, such as a static force experienced when the tool is pressing against an obstruction, can cause the parts of a linkage or tool to flex without a detectible change in joint states, the actual position of the end effector may not match the kinematic position of the end effector, even if the kinematic position is the corrected position and the corrected position is accurate with respect to the command position. In accordance with the embodiment shown in FIG. 5, this difference in position may be used to indicate force.

At step 500, the end effector begins at position A. Although described as "positions" herein, a change in position may be a change in time in which there is no movement of the end effector. However, for ease of description, "position" is used herein to mean a change of time and/or position. At step 502, the actual position of the end effector is stored. This actual position is obtained by, for example, the tool tracking component 90. At step 504, the kinematic information for the end effector is stored. This information may be obtained, for example, via the kinematic component 92.

In accordance with an embodiment, an offset may be stored at step 506. This offset provides information regarding the difference between the kinematic information stored in step 504 and the actual position information stored in step 502. Utilizing the offset, the kinematic information and the actual position information may be registered to the same position.

At step 508, the end effector moves to position B. In step 510, the change in actual position of the end effector is calculated between the actual position of the tool at position B versus the actual position of the tool in position A. At step 512, the change in position is calculated using kinematic information obtained via the kinematic component 92. If desired, although not required, another offset may be determined at position B. At step 514, the force on the tool is represented by the difference between the change in actual positions between A and B and the change in kinematic positions between A and B. The difference between the change in actual position and the change in kinematic position is utilized to represent direction and amount of force applied to the end effector, for example, supplied by contact of the end effector with body parts.

The amount of force deflection is a function of the flexibility of the tool and/or linkage, and the distance from where a force is applied to the end effector to the exit of the cannula (body port entry). This information may be utilized to generate real force metrics using known formulas. However, a user may also be interested in a change in force, and relative differences may be informative as to the amount of force being applied.

Figure 6:
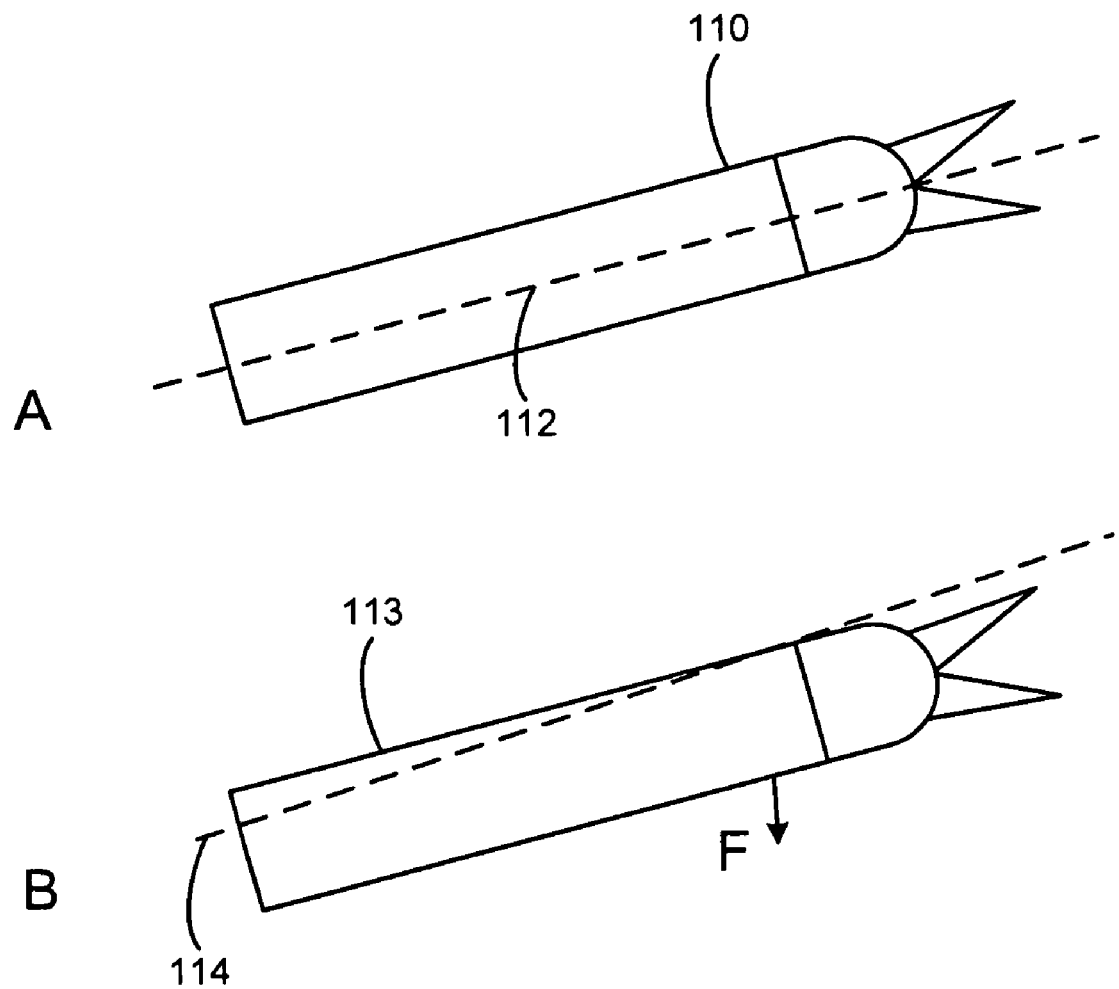
FIG. 6 is a diagrammatic representation of movement of an end effector between positions A and B with force F resisting the movement.

As an example, FIG. 6 is a diagrammatic representation of movement of an end effector from position A to position B with force F resisting the movement. At position A, an image of an end effector 110 has an actual position shown by the solid outer line for the end effector. Kinematic information (in this example, the corrected position) for the end effector is represented by the dotted line 112. In the diagram shown in the drawing, the kinematic position information matches the actual position information. In reality, however, as described above, the kinematic position information may vary to some degree, and may not match unless the offset provided in step 506 is utilized. For this example, it is assumed that the offset is used or that the kinematic information matches the actual information exactly at position A. Thus, the dotted line 112, representing the kinematic position information provided by the kinematic component 92, matches the position of the image 110 of the end effector, representing actual position information provided by the tool tracking component 90. In addition, in an embodiment, the actual position may be represented by a video of the tool.

At position B, the actual position of the end effector, represented by the image 113, is shown as being moved from position A. This actual position, as described above, is calculated by the tool tracking component 90 (e.g., at a frame rate less than or equal to approximately thirty frames per second). The kinematic position information, estimates (e.g., at an update cycle time of approximately 1333 Hz), however, that the tool, in movement from position A to position B, is now at the dotted line 114 shown with position B. The dotted line 114 represents a position where the end effector would be if moved without force being applied to the end effector 110. Absent force being applied to the end effector, this estimate is typically accurate. Although, as described above, kinematic position information is typically not accurate for determining a position of an end effector in space at a start of a process, the kinematic position information typically is accurate in determining a change in position of an end effector if there is no force.

The position shown by the dotted line 114 assumes that the beginning point of movement for the end effector, with respect to the kinematic component 92, is the line 112. If the kinematic position information did not match the actual position information at position A, then the offset provided in step 506 may be utilized at position B to project the relative position of the dotted line 114 assuming a start at line 112.

The dotted line 114 is in a different location than the actual position of the end effector due to the difference between the kinematic position information and the actual position information. The difference between the two is due to force applied to the end effector in the movement from position A to position B. For example, in the example shown in FIG. 6, a force F is applied to the end effector during movement. This force prevents the end effector from moving fully as estimated by the kinematic component 92, shown by the dotted line 114. Instead, the combination of the movement of the linkage for the end effector 110 and the force F results in the end effector being positioned as shown by the image 113 in FIG. 6B.

The force output 96 provided by the change in kinematic position information versus actual position information may be useful for a variety of different applications. For example, the force output 96 may be forwarded to the vision cart 80, which in turn may generate instructions for the surgeon console 30 to create tactile feedback to the surgeon S so that the surgeon is provided positive feedback of the existence of force. In addition, in accordance with an embodiment and as is described above with reference to FIG. 6, the force output 96 may be utilized to generate an image representing force applied to the end effector. For example, by displaying the diagram at the B portion of FIG. 6, a representation of force applied on the end effector is provided. That is, providing the visual image of where the end effector would be absent force (i.e., the dotted line 114), and simultaneously displaying the image 113 of the actual location of the end effector, a viewer is provided a visual representation of the force applied to the end effector and the force's effect on the end effector.

In an embodiment, the force output 96 may be combined with other information, such as the length the tool is inserted into the body and tool properties (e.g., via finite element analysis) to calculate the actual force that is applied on the tool. As can be understood, the amount of deflection of a tool is directly related to how much of the tool is available for flexion. The insertion length of the tool beyond cannula (body wall entry port) to the tip of the tool is readily available from a robotic system. This length, together with a measured deflection can be used to derive another quantity which is invariant to insertion length. This quantity is one step closer to the real force, and therefore can be more intuitive to use. The other factors (such as instrument properties) do not typically change at different instances so surgeons can adapt to them. This new quantity can be displayed by modulating the amount of deflection (for example, if the insertion length is small, increase the amount of actual deflection). The exact modulation can follow some finite element analysis. In general, however, the force output 96 is useful in that it provides relative force that may be useful as feedback to a surgeon S.

In an embodiment, the timing of the position A may be selected by the computer 82. As an example, the position A may be initiated by an event, such as closing of grippers or scissors. Alternatively, the position A may be selected by a user, such as the surgeon S. For example, the process above may be initiated by a surgeon, for example by the surgeon touching a foot pedal or double-clicking the master grips of the master controller when at position A so as to start the process. The surgeon's initiation sets position A. After force measurement or reaching position B, a normal mode can be returned by another touch or double-click. In an alternative embodiment, the process may be automated so that it occurs regularly. If desired, the position A may be some combination of an event, information that is available to the image capturing device 50, taken at regular intervals, or any combination of these. The amount of time elapsed before establishing position B may also be determined by time, information available, or may be requested by the surgeon S.

As an example, a surgeon may grasp an organ or other part of the patient's body with a grasper. Position A may be initiated by the surgeon just prior to or as grasping the organ. The grasper may then register the position B reading, or the surgeon may pull against the organ, and position B may be registered after some pulling. Position B may be selected after a particular amount of time, or it may be selected by the surgeon as desired. In addition, if desired, force output provided by the embodiments described herein may be output as a result of a particular force being applied to the organ. This force output may initiate a warning or other indicator to the surgeon, for example.

As described above, the force information derived from the method of FIG. 5 often is directed to the flexion of a tool or the linkage. An advantage of the method is that the force information is typically not impacted by the body wall forces, whereas many joint sensors are. In addition, unlike tip force sensors, the method in FIG. 5 may sense forces along an instrument shaft (typically a Z-axis), assuming the shaft is not parallel to the viewing angle.

The display provided herein, for example, as shown in FIG. 6B, may be useful in displaying visual information about force, regardless of the force input. That is, the display may be used to display force sensed or otherwise provided from sources other than the computer 82. Alternatively, the force information described above may be combined with additional force sensing or other force information to provide more accurate information about force.

As an example of a different source of force information, active force sensors may be utilized to determine the force on an end effector. This force may be displayed on the display 84 without the need for kinematic information. Such sensors may be, for example, located at the tip of a tool (i.e., at the end effector). The force information, as another example, may be derived from strain gauge measurements on linkages in the slave manipulator manipulating the tool that is being monitored, or it may be derived from encoders associated with joints in the slave manipulator manipulating the tool that is being monitored. Such systems for providing force information are disclosed, for example, in U.S. Pat. App. Pub. No. US 2008/0065111 A1 (filed Sep. 29, 2007), entitled "Force Sensing for Surgical Instruments."

As another example, force may be calculated using the kinematic error information described above. In one example, the change between the encoder-detected position and the corrected position may be assumed to represent force. Since forces applied to the tool, such as a static force experienced when the tool is pressing against an obstruction, can create a joint position error, an assumption can be made that the difference between the two positions is a result of force on the tool. Typical processing to generate the force information may include filtering and/or gain adjustments. As another example, the force may be extracted from the torque information generated to correct joint errors. Such systems for providing force information are disclosed in U.S. Pat. App. Pub. No. US 2005/0200324 A1 (filed Mar. 30, 2005), entitled "Non-Force Reflecting Method for Providing Tool Force Information to a User of a Telesurgical System."

If alternative force information is used as described above, in an embodiment, the actual force on the tool may be extracted by mathematically removing other forces, such as body wall forces and the like. This information may be calculated, for example, by using such information as the length the tool is inserted into the body and tool properties (e.g., via finite element analysis) to extract the actual force that is applied on the tool.

Figure 7:
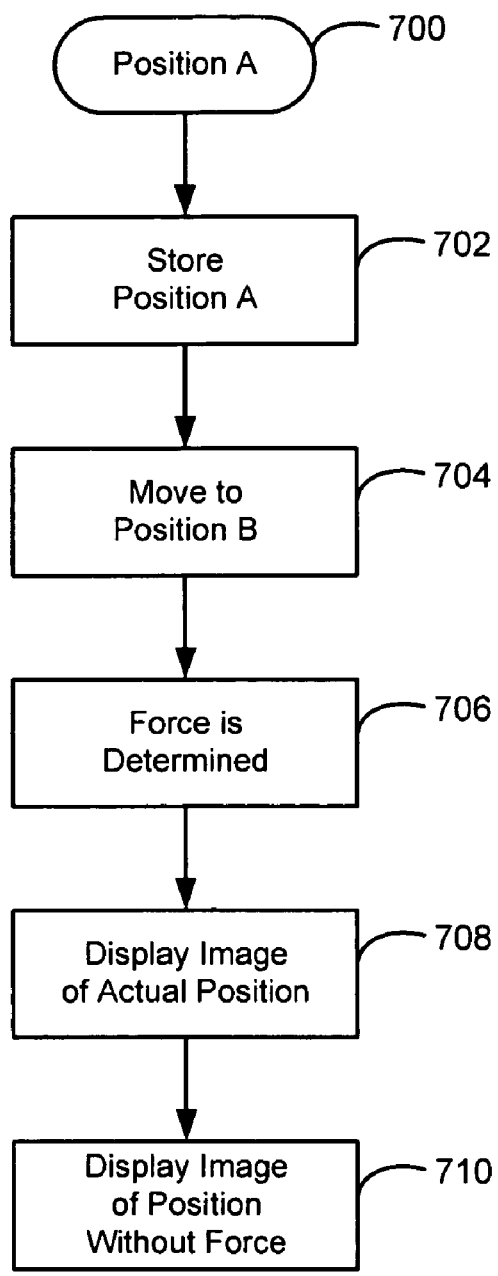
FIG. 7 is a flowchart representing steps for displaying force in accordance with an embodiment.

FIG. 7 is a flowchart representing steps for displaying force in accordance with an embodiment. At step 700, an end effector begins at position A. At step 702, the position of A is stored. At step 704, the end effector is moved to position B. At step 706, the force applied to the end effector in the movement between position A and B is determined, for example by one of the methods described above or by other methods. At step 708, an image representing the actual position of the end effector at position B is displayed. This image may be a video view of the actual end effector or another suitable image, such as a synthetic representation of the end effector. At step 710, an image representing the end effector without force being applied is displayed. This displayed image may be the dotted line 114 shown in FIG. 6B or any other appropriate image. As an example, the display in step 710 may display force in a particular direction. Force information may be provided on or near the end effector, or may be positioned in a different location, such as in another window. In any event, a user may be provided a visual or other (e.g., audible) indication of force that is applied to the end effector.

The features described herein may be provided in stereoscopic vision so that a user may visualize force in apparent three-dimensional form. As can be understood, in a stereoscopic view, force that is transverse to a direction of view is more visual in such a representation, and force that is parallel to a direction of view may not be displayed, and feedback for forces in these directions may be provided by other mechanisms, such as haptic or a different type of screen display.

In addition, in accordance with an embodiment, the force information provided above may be provided with other force information, such as sensed force information, to provide a more detailed analysis of force being applied to an end effector.

Synthetic Model to Show Force

Figure 8:
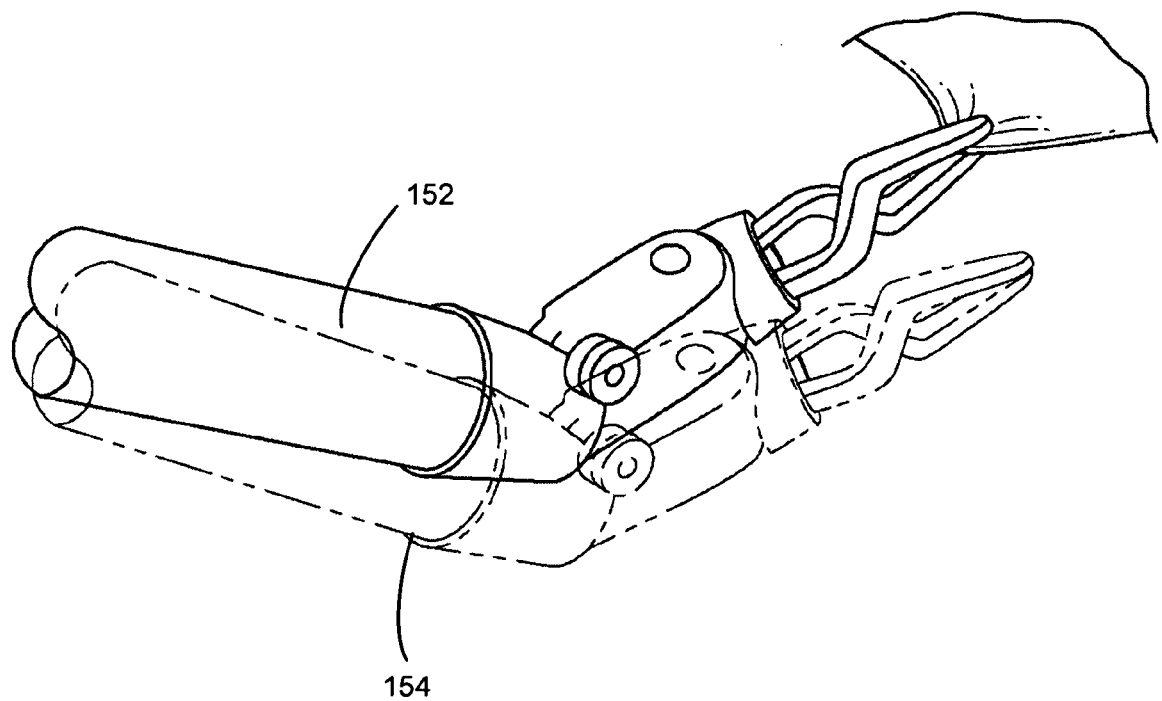
FIG. 8 is a side perspective view of an end effector and synthetic representation of an end effector showing force in accordance with an embodiment.

In accordance with an embodiment, instead of the dotted line 114, a synthetic image of an end effector may be displayed as a representation of the actual end effector without load. To this end, modeling data 150 (FIG. 3) may be provided that is associated with the patient side cart 40 and/or the computer 82. The modeling data 150 may be, for example, a two-dimensional or three-dimensional image of the end effector. In an embodiment, such an end effector is a three-dimensional model of the end effector and thus may represent an actual solid model of the end effector. The modeling data 150 may be, for example, CAD data or other three-dimensional solid model data representing an end effector, such as the end effector 152 shown in FIG. 8. In an embodiment, the three-dimensional model is manipulatable at each joint so that movements of the end effector 152 may be mimicked by a synthetic model 154 (shown in phantom line in FIG. 8) of the end effector. As shown in FIG. 8, the synthetic model 154 may be the same size as the image of the actual end effector 152, but it may be larger or smaller.

Although shown in dashed lines in the drawings, the synthetic model 154 may be represented in a number of different ways. As an example, the synthetic model 154 may be a transparent image of the end effector 152 or a wire diagram image of the end effector. The synthetic model 154 may alternatively be an image that is not transparent, but such a model may make viewing of the actual end effector 152 difficult.

Figure 9:
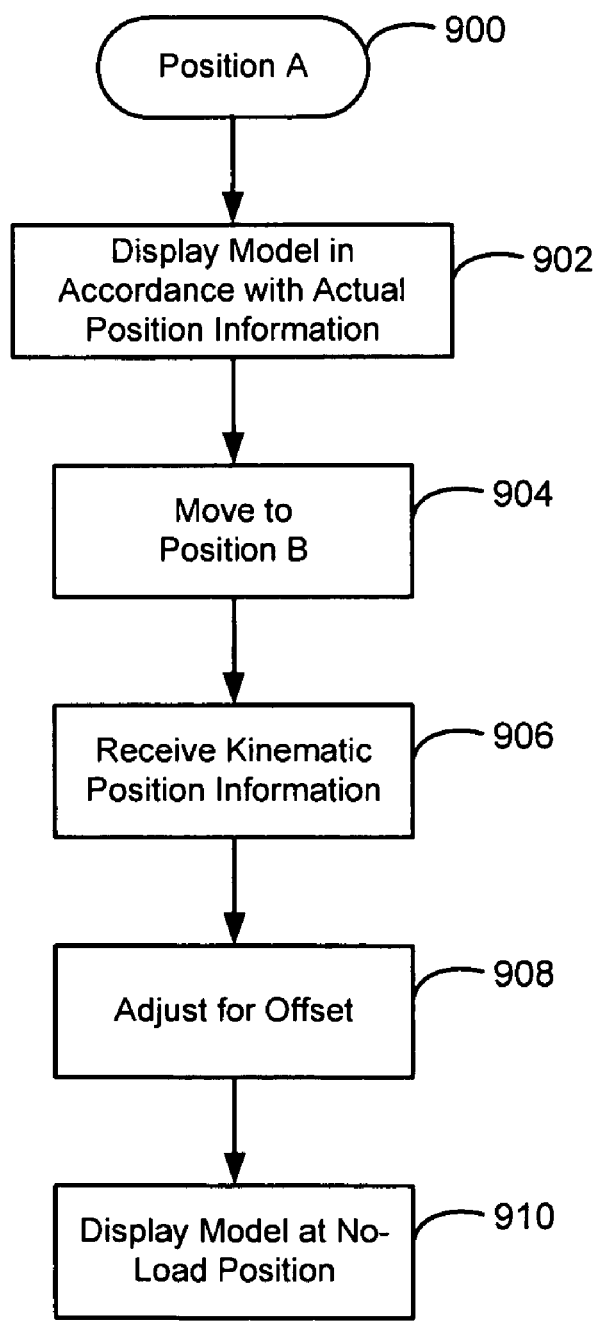
FIG. 9 is a flowchart representing steps for displaying a synthetic model in accordance with an embodiment.

FIG. 9 is a flowchart representing steps for displaying the synthetic model 154 in accordance with an embodiment. In step 900, the end effector 152 begins at position A. In the embodiment shown in FIG. 9, the synthetic model is displayed in accordance with the actual position information (i.e., is displayed at the actual position of the end effector 152) at step 902. Thus, the synthetic model is superimposed over the image of the end effector 152, which may be a video image of the end effecter. For example, as shown in FIG. 8, the synthetic model 154 is translucent or transparent and may be displayed over the video image of the actual end effector 152. As another option, the synthetic model 154 may start at a location other than the actual position of the end effector 152.

At step 904, the end effector moves to position B. At step 906, kinematic position information is received for the end effector 152. An adjustment for offset is taken at step 908, and then the synthetic model 154 is displayed in step 910.

In accordance with the method in FIG. 9, the synthetic model 154 may continue to be updated so that force information is represented by the synthetic model 154 and its position relative to the end effector 152. In the display shown, the end effector 152 is a video image of the end effector. As such, steps 906-910 may be updated in real time, for both the video image and the synthetic model 154, so that the synthetic model 154 and its position are updated as the end effector 152 is moved. In such continual real time display of the synthetic model 154, step 902 may be substituted with the display of the model at the last location instead of the actual position. In addition, as described above, the offset and the original position A may be determined in accordance with an event or timing or in another manner.

In accordance with an embodiment, the methods described herein may be altered so as to control the display of forces as the surgeon desires. For example, when a movement is made between two positions, there may be a number of other forces involved other than force on the tip of the tool, such as body cavity contact or gravity, that the surgeon does not want to affect his or her measurement. This problem may be even more pronounced when the distance over which the end effector is moved between positions A and B is increased.

In general, the forces that the surgeon desires to measure during a movement of an end effector between two positions are the forces at the tip of the tool, i.e., at the end effector. In an embodiment, the force measurements are taken so that they filter out, to the extent possible, forces other than those applied at the end effector. One method for eliminating other forces, such as body wall forces and gravity, is by assuming that total movement between the two positions, which indicates total forces on the tool between the two positions, is a combination of two sets of forces: those applied at the tip of the tool and other forces. In general, body forces, gravity, and other forces that are remote of the tip may be detected by the encoders 102. As described above, as part of the setup process and movements for a patient side cart and the corresponding robotic manipulator arm, the arm is instructed to move and the encoders 102 determine whether the encoder-detected position is consistent with the command position. If not, then the manipulator is instructed to move to the corrected position. As discussed above, this movement to the corrected position may be used to calculate force exerted during the movement. This joint correction will address joint error, but typically it does not address flexing of the components of the linkage. Assuming that flexing of the tool at the tip is the primary form of force absorption at the tip, then, in accordance with an embodiment, any force not sensed through the joint correction process may be assumed to be force applied at the tip. Thus, in accordance with an embodiment, the forces exerted at the tip are determined by subtracting the calculated joint forces from the total forces.

Figure 11:
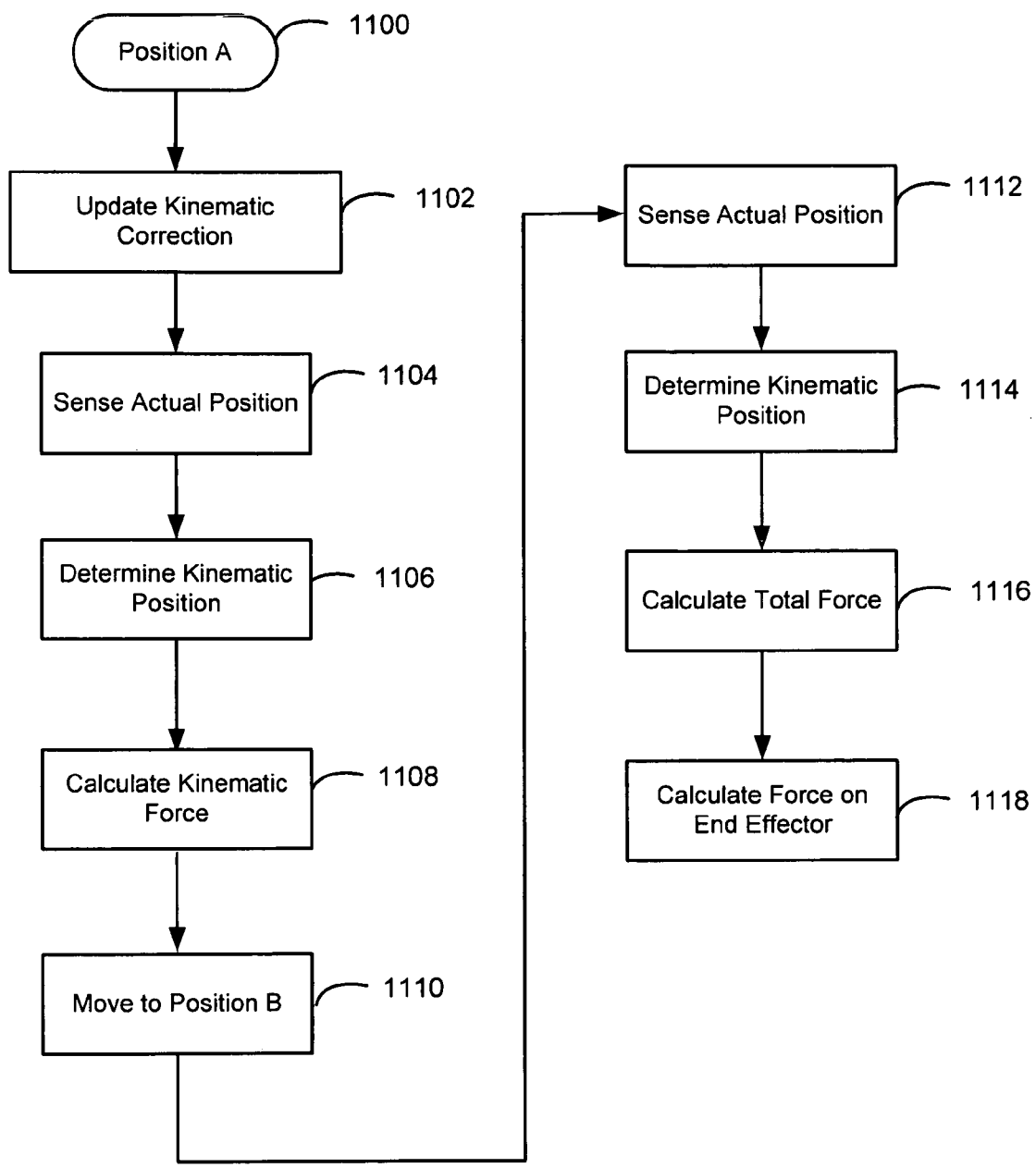
FIG. 11 is a flow chart representing steps for filtering forces to limit force measurements primarily to tip forces in accordance with an embodiment.

FIG. 11 is a flow chart representing steps for filtering forces primarily to tip forces in accordance with an embodiment. Beginning at step 1100, and end effector is at position A. At step 1102, the kinematic correction for the linkage is updated. At step 104, the actual position of the end effector is sensed, for example using the tool tracking component 90. At step 1106, the kinematic position is calculated for position A. At step 1108, a kinematic force calculation is made at position A using the kinematic information, as described above. At step 1110, the tool is moved to Position B. At step 1112, the actual position of the tool is sensed, for example using the tool tracking component 90. At step 1114, the kinematic position is calculated for position B. At step 1116, a force calculation is made of the movement from A to B using a kinematic position of the end effector verses an actual position of the end effector, for example as described above with reference to FIG. 5. At step 1118, the force on the end effector is calculated by subtracting the force in step 1112 from the total force from step 1116.

In the force calculation of step 1118, the force on the tool tip is calculated based upon a difference between the total force and kinematic joint forces. As described above, the kinematic joint forces are assumed to represent the forces other than tip forces. If desired, all three forces (total, kinematic, or tip) or any subset of these three may be generated as the force output 96, and/or may be displayed to a user, for example on the display 84 or the viewer 32, as indicated by the dotted line in FIG. 4. In this calculation, it is assumed that other, outside forces are held constant between positions A and B, and the motion between these two positions is due to the application of force.

Methods described herein are advantageous in that they provide instantaneous visual feedback to a surgeon of force on a tool. A surgeon utilizing the features may grow accustomed to the intuitive feedback, and may recognize tile amount of force being used by comparing the current displacement to a history of procedures. For example, a surgeon performing a sewing procedure who sees a deflection of X may recognize that he or she is applying roughly the same force when a deflection of X occurs in a different procedure.

If desired, the amount of deflection may be altered for stiff tools so that a visual representation of the deflection is exaggerated on the display. In addition, if desired, force may be displayed by showing force information in a different manner. For example, an arrow indicating a direction of force may be used, or a synthetic representation may be displayed in another direction or position.

In another aspect of the invention, the tip force information may be used to derive the deformation, or elasticity, of tissue that is clinically relevant. For, e.g., tumors on or below the tissue surface, surgeons can directly sense the difference in elasticity between normal and cancerous tissues by applying pressure to the two different types of tissue and using intuitive visualization of instrument tip flexing (described above) to determine deformation characteristics of particular locations on the tissue. For a given amount of movement by an end effector into contact with the tissue, the amount that the end effector actually moves when in contact with the tissue, instead the end effector flexing, is directly related to the deformation of the tissue. Thus, force information, as determined above, may be used to determine deformation of a tissue. Moreover, other force information, such as provided by sensors, may be used to determine tissue deformation. For example, the amount a tissue pushes back against an end effector will be reflected in the force sensed by active sensors—the more force sensed, the less the tissue is deforming. In addition, the force information, such as may be extracted about the instrument tip, may be combined with, e.g., ultrasound imaging to provide elasticity imaging of tissues and organs underneath the tissue with absolute elasticity measurements.

In an embodiment, the display of tissue may be altered to show tissue deformation. This deformation may be calculated, for example, based upon force input from any number of sources, including, but not limited to, the sources listed herein. Based upon the amount of force that is sensed, the deformation display may be altered accordingly. For example, in an embodiment, the tissue at an impact point, for example where grasped or where an end effector applies pressure, may be altered in color, for example shaded variations in color based upon the amount of force applied to the tissue. The tissue's point of impact can be determined from the location of touching tool tip that is tracked by tool tracking. The surrounding tissue surface locations (left and right) for overlaying deformation color can be obtained by sparse tissue matching and/or regular dense stereo matching constrained in the selected region of interest. The color and/or intensity of the color may be altered based upon the sensed tip force or tissue elasticity using existing mechanical models. This information may be helpful, for example, in providing visual feedback to a surgeon of force applied to particular tissue.

Figure 12:
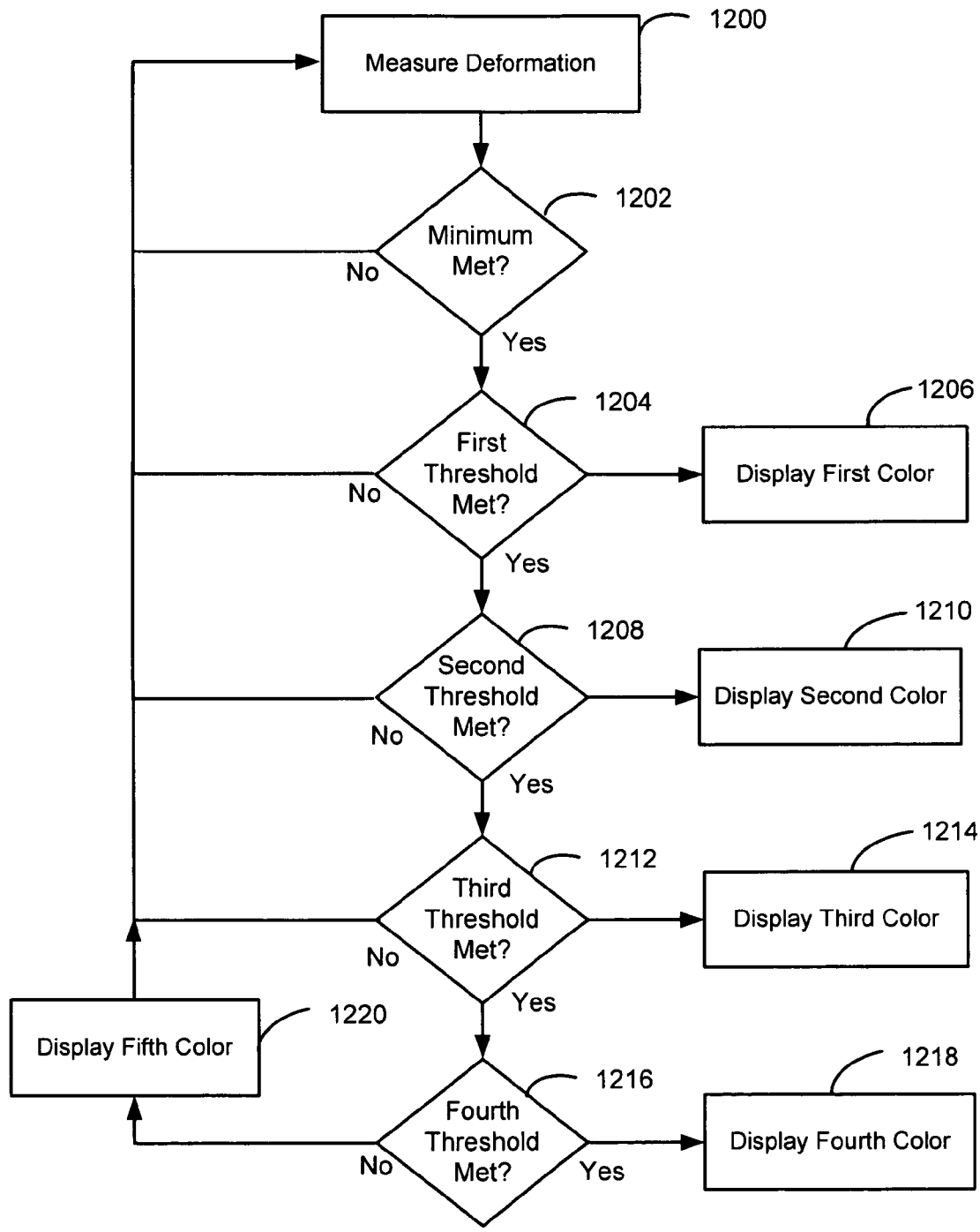
FIG. 12 is a flow chart representing steps for displaying deformation of a tissue using variations in color in accordance with an embodiment.

For example, in FIG. 12, a method is shown for displaying deformation of a tissue using variations in color in accordance with an embodiment. Beginning at step 1200, deformation is measured for a tissue, for example using the methods described above. At step 1202, a determination is made whether a minimum deformation threshold is met. This determination represents a minimum amount of deformation in which to display an indication of deformation for the tissue. If the threshold is not met, then the process continually loops back to 1200. If this threshold is met, then the process proceeds to step 1204, where a determination is made whether a first deformation threshold has been met, and if so, a first color is displayed at step 1206. In the embodiment shown in the drawings, for simplicity, this first deformation represents a maximum deformation permitted for the tissue, and thus the color may indicate such a high deformation, for example using the color red. If this first deformation is not met, then step 1204 branches to step 1208, where a determination is made whether a second deformation threshold has been met, the second deformation being less than the first deformation. If so, then a second color is displayed at 1210. Additional determinations are made, and colors applied as needed, in steps 1210 to 1218, where the amount of deformation needed to meet a threshold continues to decline to the minimum or until the necessary color is displayed. If a fourth threshold is not met, then step 1216 branches to step 1220, where a fifth color is displayed. This color represents a minimum deformation displayed by the system. The process shown in FIG. 12 may continue to loop back, so that changes in deformation are reflected by different color variations.

In the embodiment shown in the drawings, the number of different colors displayed is five, although any number may be used. In addition, if desired, a color may be altered, such as lightened or darkened, based upon an increase or decrease in deformation.

Using the process of FIG. 12, a surgeon is provided visual feedback of deformation of tissue. The amount of deformation may reflect a type of tissue and/or the condition of the tissue. Although described herein as being displayed as a color or color variation displayed on the tissue, deformation information may be provided in another manner or in another location.

In accordance with another embodiment, a tissue may be varied in color based upon how far the tissue is from an impact point. That is, the tissue may be one color at the impact point and different colors as the tissue is spaced from the impact point. The variations in color represent different amounts of deformation at the different locations. To determine a color for a particular region, other techniques, such as robust image matching or stereo matching, such as is disclosed in U.S. Pat. App. No. 61/204,082(filed Dec. 31, 2008), may be incorporated to determine deformation at particular locations, including the impact point and locations spaced from the impact point.

Other variations are within the spirit of the present invention. Thus, while the invention is susceptible to various modifications and alternative constrictions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of providing force information for a robotic surgical system, the method comprising:
    storing first kinematic position information and first actual position information for a first position of an end effector, the first kinematic position information being based on joint states of a linkage used to support the end effector, the first position selected by either a user of the robotic surgical system or based upon an event;
    storing second kinematic position information and second actual position information for a second position, the second kinematic position information being based on joint states of a linkage used to support the end effector; and providing force information regarding force applied to the end effector at the second position utilizing the first actual position information, the second actual position information, the first kinematic position information, and the second kinematic position information.

2. The method of claim 1, wherein the force information is derived from a positional difference between a change between the first actual position information and second actual position information and a change between the first kinematic position information and the second kinematic position information, the force information comprising a difference in force applied to the end effector between the first and second positions.

3. The method of claim 2, further comprising calculating an offset between the first kinematic position information and the first actual position information, and utilizing the offset at the second position in the derivation of the force information.

4. The method of claim 1, wherein the second position is selectable by a user of the robotic surgical system.

5. The method of claim 1, wherein the first actual position information and the second actual position information each comprise visual information about the position of the end effector.

6. The method of claim 1, further comprising displaying a representation of force utilizing the force information.

7. The method of claim 6, wherein displaying a representation of force comprises displaying (1) a first image representing the second actual position information and (2) a second image representing the second kinematic position information.

8. The method of claim 7, wherein the second image comprises a visual representation of the end effector.

9. The method of claim 7, wherein the first image comprises a video image of the end effector.

10. The method of claim 7, wherein the second image comprises a visual representation of the second kinematic information.

11. The method of claim 10, wherein the displaying a representation of force comprises displaying the representation of force on a viewer of a surgeon console of the robotic surgical system.

12. The method of claim 10, wherein the visual representation comprises a synthetic representation of the tool.

13. The method of claim 12, wherein the synthetic representation comprises a model of the tool.

14. The method of claim 13, wherein the model comprises a three-dimensional model of the tool.

15. The method of claim 6, wherein the displaying a representation of force comprises displaying the representation of force on a viewer of a surgeon console of the robotic surgical system.

16. The method of claim 15, wherein the second image comprises a visual representation of the end effector.

17. The method of claim 15, wherein the displayed representation of force comprises a video image of the end effector.

18. The method of claim 1, wherein the force information is filtered to focus on forces applied at or adjacent the end effector.

19. The method of claim 18, further comprising:
determining joint errors from positions of the joints with respect to a commanded position of the joints;
correcting the joints toward the command position; and
utilizing the correction of the joints to filter the force information.

20. The method of claim 19, wherein the correction of the joints is utilized to generate second force information, and wherein filtering the force information comprises subtracting the second force information.

21. The method of claim 1, wherein the force information is combined with additional force information.

22. The method of claim 21, wherein the additional force information comprises information derived from active force sensors.

23. The method of claim 22, wherein the active force sensors comprise force sensors located at the end effector.

24. The method of claim 22, wherein the linkage comprises one or more joints, and wherein the active force sensors comprise sensors located at the one or more joints.

25. The method of claim 22, wherein the linkage comprises joints, the method further comprising:
determining joint errors from positions of the joints with respect to a commanded position of the joints;
correcting the joints toward the command position; and
wherein the additional force information comprises information derived from the correcting of the joints.

26. The method of claim 1, wherein the linkage comprises joints, and wherein the kinematic position information comprises information about joint states of the linkage.

27. The method of claim 26, further comprising:
determining joint errors from positions of the joints with respect to a commanded position of the joints; and
correcting the joints toward the command position to a corrected position; and
wherein information about joint states of the linkage comprises information about the joints at the corrected position.

28. An assembly for providing force information within a robotic system, the assembly comprising:
a user selection component for selecting one or more positions of an end effector at which kinematic and actual position information of the end effector are to be determined;
means for determining the kinematic position information from joint states of a linkage while the linkage supports the end effector;
means for determining the actual position information; and
means for visually providing force information regarding force applied to the end effector, the force information being provided in response to the kinematic position information and the actual position information.

29. The assembly of claim 28, wherein the force information is combined by the means for visually providing force information with additional force information.

30. The assembly of claim 29, wherein the additional force information comprises information derived from one or more active force sensors.

31. The assembly of claim 30, wherein the one or more active force sensors comprise one or more force sensors located at the end effector.

32. The assembly of claim 20, wherein the linkage comprises one or more joints, and wherein the one or more active force sensors comprise one or more sensors located at the one or more joints.

33. The assembly of claim 29, wherein the linkage comprises joints, and wherein the additional force information comprises information derived from correcting of the positions of the joints.

34. The assembly of claim 28, wherein the means for determining actual position information receives a video feed from an image capture device.

35. The assembly of claim 28, wherein the means for visually providing force information includes a display component for displaying a representation of force utilizing the force information.

36. The assembly of claim 35, wherein the display component is configured to display a representation of force comprising (1) a first image representing the actual position information and (2) a second image representing the kinematic position information.

37. The assembly of claim 36, wherein the second image comprises a synthetic representation of the tool.

38. The assembly of claim 37, wherein the synthetic representation comprises a model of the tool.

39. The assembly of claim 38, wherein the model comprises a three-dimensional model of the tool.

40. The assembly of claim 28, further comprising a filter to focus the force information on forces applied at or adjacent the end effector.

* * * * *